US012583751B2

(12) United States Patent
Hwang et al.

(10) Patent No.: US 12,583,751 B2
(45) Date of Patent: Mar. 24, 2026

(54) REDUCED ACYLATED GRAPHENE OXIDE AND METHOD FOR PREPARING THE SAME

(71) Applicant: KOREA INSTITUTE OF ENERGY RESEARCH, Daejeon (KR)

(72) Inventors: Seung Hae Hwang, Daejeon (KR); Chang-soo Jin, Sejong-si (KR); Kyoung-hee Shin, Daejeon (KR); Sun-hwa Yeon, Sejong-si (KR); Se-Kook Park, Daejeon (KR); Dong Ha Kim, Daejeon (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 707 days.

(21) Appl. No.: 17/986,174

(22) Filed: Nov. 14, 2022

(65) Prior Publication Data

US 2023/0150822 A1     May 18, 2023

(30) Foreign Application Priority Data

Nov. 18, 2021     (KR) ........................ 10-2021-0159089

(51) Int. Cl.
*C01B 32/184*          (2017.01)
*B82Y 30/00*          (2011.01)
(Continued)

(52) U.S. Cl.
CPC ............ *C01B 32/184* (2017.08); *C07C 45/61* (2013.01); *H01M 4/663* (2013.01); *B82Y 30/00* (2013.01); *B82Y 40/00* (2013.01)

(58) Field of Classification Search
CPC ..... C01B 32/184; C01B 32/192; C01B 32/23; C01B 32/194; C01B 32/182; C01B 32/186; C01B 32/188; C01B 32/19; C01B 32/196; C01B 32/198; C07C 45/61; H01M 4/663; H01M 4/587; H01M 10/0525; H01M 2004/027; B82Y 30/00; B82Y 40/00;
(Continued)

(56) References Cited

FOREIGN PATENT DOCUMENTS

| CN | 110223854 A | 9/2019 |
| KR | 10-2013-0010832 A | 1/2013 |

(Continued)

OTHER PUBLICATIONS

Seifvand, et al., Novel TiO2/graphene oxide functionalized with a cobalt complex for significant degradation of NOx and CO, RSC Adv. 2015; 5: 93706-93716 (Year: 2015).*

(Continued)

*Primary Examiner* — Daniel C. McCracken
(74) *Attorney, Agent, or Firm* — Birch, Stewart, Kolasch & Birch, LLP

(57)          ABSTRACT

Provided are reduced acylated graphene oxide as an electrode active material and a method for preparing the same. By the method for preparing reduced acylated graphene oxide according to the present invention, a negative electrode active material for a lithium secondary battery having stable activity and a high battery capacity may be prepared with a simple and low-cost process. In addition, the active material prepared by the preparation method has low resistance, a high battery capacity, and improved rate-limiting characteristics while having stable cycle characteristics.

5 Claims, 14 Drawing Sheets

(51) Int. Cl.
    B82Y 40/00       (2011.01)
    C07C 45/61       (2006.01)
    H01M 4/66       (2006.01)

(58) Field of Classification Search
    CPC ..... Y02E 60/10; B01J 19/126; C01P 2002/72;
             C01P 2006/11; C01P 2006/12; C01P
                                    2006/14
    See application file for complete search history.

(56)             References Cited

FOREIGN PATENT DOCUMENTS

| KR | 10-1245815 | B1 | 3/2013 | | |
|----|------------|----|--------|---|---|
| KR | 10-1486760 | B1 | 1/2015 | | |
| KR | 10-2015-0118744 | A | 10/2015 | | |
| KR | 10-1643136 | B1 | 7/2016 | | |
| KR | 10-2040075 | B1 | 11/2019 | | |
| WO | 112164771 | | * | 1/2021 | .............. H01M 4/36 |

OTHER PUBLICATIONS

ThermoFisher Scientific Safety Data Sheet Imidazole, pp. 1-8 (2021) (Year: 2021).*
Machine Translation of CN 112164771 (Year: 2021).*
Mohammadi-Arbati et al., "Efficiency Beyond 6% in P3HT:PCBM Photovoltaics via Simultaneous Addition of poly(3-hexylthiophene) based Grafted Graphenic Nanosheets and Hydrophobic Block Copolymers", Mar. 2019, pp. 1-28.
Nordenström et al., "Acetylation of graphite oxide", Phys. Chem. Chem. Phys., 2020, vol. 22, pp. 21059-21067.
Nordenstrom et al., "Acetylation of graphite oxide," Phys. Chem. Chem. Phys., vol. 22, 2020, pp. 21059-21067.

* cited by examiner

REDUCED ACYLATED GRAPHENE OXIDE AND METHOD FOR PREPARING THE SAME

CROSS-REFERENCE TO RELATED APPLICATIONS

This application claims priority under 35 U.S.C. § 119 to Korean Patent Application No. 10-2021-0159089, filed on Nov. 18, 2021, in the Korean Intellectual Property Office, the disclosure of which is incorporated herein by reference in its entirety.

TECHNICAL FIELD

The following disclosure relates to reduced acylated graphene oxide, a method for preparing the same, a lithium secondary battery using the reduced acylated graphene oxide as a negative electrode active material, and a redox flow battery and a lithium-air battery using the reduced acylated graphene oxide as an electrode.

BACKGROUND

Due to concerns about global climate change related to greenhouse gas emissions and other types of pollution, a policy to encourage the use of electric vehicles instead of internal combustion engines is being implemented. Since an electric vehicle is driven with energy from a battery, unlike a conventional internal combustion engine vehicle, a built-in battery should satisfy high-energy density and high output characteristics. Among many batteries satisfying the characteristics, a lithium secondary battery has the closest characteristics to them.

As the capacities of a positive electrode and a negative electrode are increased and efficiency is higher as main constituents, a lithium secondary battery having high energy density may be implemented. Among the materials, graphite is widely used as a negative electrode active material since it has reversible charge and discharge characteristics by forming an intercalation compound ($LiC_6$) with lithium. However, since graphite has a limited lithium ion storage space in an $sp^2$ carbon structure and has a theoretical lithium storage capacity of about 370 mAh/g, there is limitation in implementing a high energy density lithium secondary battery.

Development of a non-carbon-based negative electrode active material based on silicon or tin having a higher theoretical capacity than a carbon-based material is in progress for the higher capacity of a negative electrode, but the non-carbon-based negative electrode active material shows a serious volume change when reacting with lithium as compared with a carbon-based material, and thus, has a disadvantageous aspect in an energy storage device requiring a long life time.

Accordingly, there is still needed to develop a new carbon-based material for increasing a lithium storage capacity and also improving rate-limiting characteristics, and simultaneously using a carbon-based material showing stable life characteristics with a small volume change. A carbon-based material satisfying the characteristics as such may be used as a high-capacity, high-output, and low-resistance electrode for a positive electrode conductive material, a redox flow battery, and a lithium-air battery as well as a lithium secondary battery negative electrode active material.

SUMMARY

An embodiment of the present invention is directed to providing a negative electrode active material for a lithium secondary battery having low resistance, a high battery capacity, and improved rate-limiting characteristics while having stable cycle characteristics.

Another embodiment of the present invention is directed to providing a method for preparing a negative electrode active material for a lithium secondary battery having stable activity and a high battery capacity by a simple and low-cost process.

In one general aspect, a method for preparing reduced acylated graphene oxide includes: (a) subjecting graphene oxide to an acylation reaction to prepare acylated graphene oxide; and (b) reducing the acylated graphene oxide.

In the method for preparing reduced acylated graphene oxide of the present invention, the acylated graphene oxide may be graphene oxide bound to R—C(=O)— or R—C(=O)O— (R is $C_1$ or higher alkyl or $C_5$ or higher aryl).

In the method for preparing reduced acylated graphene oxide of the present invention, the reducing of (b) may be performed in the presence of a solid reducing agent, the solid reducing agent may be carbonaceous powder, and the carbonaceous powder may be carbon black.

In the method for preparing reduced acylated graphene oxide of the present invention, the reducing of (b) may be performed by irradiating a mixture of the acylated graphene oxide and the reducing agent with microwaves.

In another general aspect, reduced acylated graphene oxide prepared from the preparation method may be provided.

In the reduced acylated graphene oxide of the present invention, the reduced acylated graphene oxide may have a maximum diffraction peak in a 2θ range of 20 to 30° in an X-ray diffraction spectrum of the reduced acylated graphene oxide. In addition, a ratio between carbon and oxygen forming the reduced graphene oxide may be 20:1 to 5:1, and a tap density may be 0.05 to 0.3 $g/cm^3$. In addition, the reduced acylated graphene oxide may have a specific surface area of 50 to 350 $m^2/g$, and a pore volume of 0.1 to 1.0 $cm^3/g$.

In another general aspect, an electrode active material includes the reduced acylated graphene oxide.

In still another general aspect, a lithium secondary battery includes: a negative electrode including the electrode active material and a conductive material; a separator disposed on the negative electrode; and a positive electrode disposed on the separator.

Other features and aspects will be apparent from the following detailed description, the drawings, and the claims.

DETAILED DESCRIPTION OF EMBODIMENTS

Figure 1:
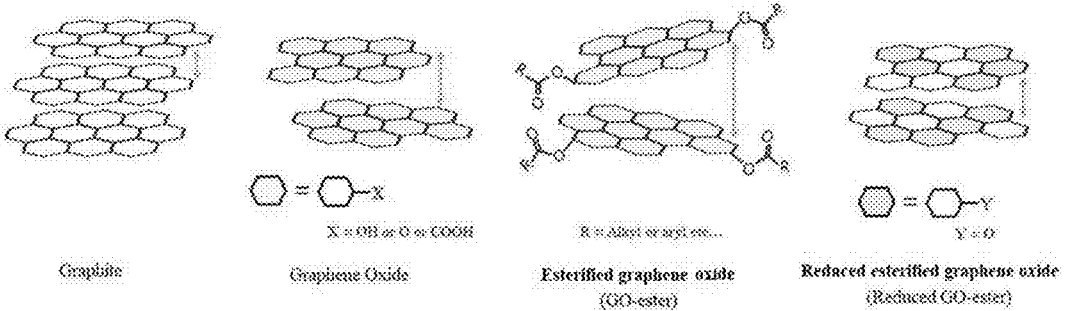
FIG. 1 is schematic diagrams showing structures of graphite, GO, AGO, and RAGO.

Hereinafter, the method for preparing reduced acylated graphene oxide of the present invention will be described in detail with reference to the accompanying drawings.

The drawings to be provided below are provided by way of example so that the spirit of the present invention can be sufficiently transferred to a person skilled in the art to which the present invention pertains. Therefore, the present invention is not limited to the drawings provided below but may be embodied in many different forms, and the drawings suggested below may be exaggerated in order to clear the spirit of the present invention.

Technical terms and scientific terms used herein have the general meaning understood by those skilled in the art to which the present invention pertains, unless otherwise defined, and the description for the known function and configuration which may unnecessarily obscure the gist of the present invention will be omitted in the following description and the accompanying drawings.

In addition, the singular form used in the specification and claims appended thereto may be intended to include a plural form also, unless otherwise indicated in the context.

In the present specification and the appended claims, the terms such as "first" and "second" are not used in a limited meaning but are used for the purpose of distinguishing one constituent element from other constituent elements.

In the present specification and the appended claims, the terms such as "comprise" or "have" mean that there is a characteristic or a constituent element described in the specification, and as long as it is not particularly limited, a possibility of adding one or more other characteristics or constituent elements is not excluded in advance.

In the present specification and the appended claims, when a portion such as a membrane (layer), a region, and a constituent element is present on another portion, not only a case in which the portion is in contact with and directly on another portion but also a case in which other membranes (layers), other regions, other constitutional elements are interposed between the portions is included.

The method for preparing reduced acylated graphene oxide of the present invention is characterized by including: (a) subjecting graphene oxide to an acylation reaction to prepare acylated graphene oxide; and (b) reducing the acylated graphene oxide.

In a specific example, the acylated graphene oxide may be graphene oxide bound to $R$—$C(=O)$— or $R$—$C(=O)O$—. Here, R may be a $C_1$ or higher aliphatic hydrocarbon (alkyl) or $C_5$ or higher aromatic hydrocarbon (aryl), preferably $C_{1\text{-}20}$ alkyl or $C_{5\text{-}20}$ aryl, but is not necessarily limited thereto. Due to $R$—$C(=O)$— or $R$—$C(=O)O$— bound to graphene oxide, a three-dimensional structure is formed in a graphene plane layer, leading to an open structure. The structure imparts an additional capacity to facilitate higher energy characteristics of active material.

In a specific example, in the step of preparing acylated graphene oxide of (a), graphene oxide and an acyl anhydride may be mixed to prepare an acylated graphene oxide dispersion. Here, a weight ratio between graphene oxide and an acyl anhydride may be 1:50 to 50:1, preferably 1:25 to 25:1.

The thus-prepared dispersion may be heat-treated at 50 to 1,500° C. for 1 to 24 hours, preferably at 80 to 800° C. for 1 to 12 hours to prepare an acylated graphene oxide mixed solution.

In a specific example, the step of reducing acylated graphene oxide of (b) may be performed in the presence of a solid reducing agent. Here, the solid reducing agent may be carbonaceous powder, and the carbonaceous powder may be carbon black. The solid reducing agent is a material which hardly expresses non-storage capacity during charging and discharging, and has an advantage of minimizing a phenomenon in which the physical properties and the electrical conductivity of an electrode are changed by the solid reducing agent, due to the use of the solid reducing agent.

A weight ratio between the acylated graphene oxide and the solid reducing agent may be 1:0.01 to 1:1, preferably 1:0.05 to 1:0.5.

In a specific example, the step of reducing acylated graphene oxide of (b) may be performed by irradiating a mixture of the acylated graphene oxide and the reducing agent with microwaves. In the process of reducing the acylated graphene oxide, a phenomenon in which the nature of the acylated graphene oxide is changed may be minimized by a rapid and short heat treatment using microwaves.

In addition, the acylated graphene oxide may be reduced by the heat treatment under a reducing atmosphere.

The reduced acylated graphene oxide of the present invention is characterized by being prepared from the preparation method.

In a specific example, the reduced acylated graphene oxide may have a maximum diffraction peak in a 20 range of 20 to 30°, preferably in a 20 range of 20 to 25° in an X-ray diffraction spectrum of the reduced acylated graphene oxide. When the reduced acylated graphene oxide has the maximum diffraction peak in the above 20 range, an irreversible capacity ratio is lowered and a capacity is increased, and openness is decreased to improve life characteristics.

In a specific example, a ratio between carbon and oxygen forming the reduced acylated graphene oxide may be 100:1 to 5:1, preferably 50:1 to 5:1. When the ratio between carbon and oxygen is in the above range, it is appropriate for implementing improvement of rate-limiting characteristics by high electronic conductivity.

In a specific example, the reduced acylated graphene oxide may have a tap density of 0.02 to 0.6 $g/cm^3$, preferably 0.03 to 0.5 $g/cm^3$, and most preferably 0.05 to 0.3 $g/cm^3$. When the tap density is in the above range, a higher volume capacity, a thinner electrode, and a short electron path may be provided for the same mass load, and thus, a volume energy density may be increased.

In a specific example, the reduced acylated graphene oxide may have a specific surface area of 10 to 500 $m^2/g$, preferably 25 to 300 $m^2/g$. When the specific surface area is in the above range, an electrode-electrolyte contact area is increased and an electrolyte ion may be rapidly diffused, and thus, it is appropriate for implementing improvement of rate-limiting characteristics, and an initial electrolyte decomposition reaction occurring in a large specific surface area is suppressed, so that an irreversible capacity loss in an initial cycle is minimized and it is advantages for long-term cycle characteristics.

In a specific example, the reduced acylated graphene oxide may have a pore volume of 0.1 to 2.0 $cm^3/g$, preferably 0.2 to 1.5 $cm^3/g$. When the pore volume is in the above range, more activity sites are provided for charge and discharge cycles to have better cycling stability.

The electrode active material of the present invention is characterized by including the reduced acylated graphene oxide. In addition, the lithium secondary battery of the present invention is characterized by including a negative electrode including the electrode active material and a conductive material; a separator disposed on the negative electrode; and a positive electrode disposed on the separator.

In a specific example, the conductive material may be carbonaceous powder, and the carbonaceous powder may be carbon black. The carbonaceous powder is a material which hardly expresses non-storage capacity during charging and discharging, and has an advantage of minimizing a phenomenon in which the physical properties and the electrical conductivity of an electrode are changed, due to the use of the carbonaceous powder.

The separator is disposed between a positive electrode plate and a negative electrode plate and electrically insulates the positive electrode plate and the negative electrode plate from each other, and may be formed in the form of a porous film so that lithium ions and the like pass through each other between the positive electrode plate and the negative electrode plate. The separator may be formed of a porous film using, for example, polyethylene (PE), polypropylene (PP), or a composite film thereof.

The lithium secondary battery may include a solid electrolyte and a liquid electrolyte solution, and the electrolyte solution may include a liquid solvent and a lithium salt. As the liquid solvent, an aprotic organic solvent may be used, and a non-limiting example of the liquid solvent may include ethylene carbonate, propylene carbonate, butylene carbonate, dimethyl carbonate, diethyl carbonate, and the like, but is not limited thereto. In addition, a non-limiting example of the lithium salt may include LiCl, LiBr, LiI, $LiClO_4$, $LiBF_4$, $LiB_{10}Cl_{10}$, $LiPF_6$, $LiCF_3SO_3$, $LiCF_3CO_2$, $LiAsF_6$, $LiSbF_6$, $LiAlCl_4$, $CH_3SO_3Li$, $CF_3SO_3Li$, $(CF_3SO_2)_2NLi$, and the like, but is not limited as long as it is easily dissolved in an electrolyte, and may be a solid electrolyte of a polymer, an oxide, and a sulfide.

The redox flow battery (RFB) of the present invention is characterized by including an electrode including the reduced acylated graphene oxide.

The electrode including the reduced acylated graphene oxide is characterized by having low resistance and a high battery capacity while having stable cycle characteristics, and the redox flow battery including the electrode has low resistance and an increased specific surface area to show high output characteristics. In addition, since the reversible electron oxidation/reduction reaction characteristics of the electrode contribute to not only the capacity of an active material in a redox flow battery but also an additional capacity, high capacity characteristics may be shown.

The lithium-air battery of the present invention is characterized by including an electrode including the reduced acylated graphene oxide.

The electrode including the reduced acylated graphene oxide is characterized by having low resistance and a high battery capacity while having stable cycle characteristics, and the lithium-air battery including the electrode has the low resistance of the electrode, so that output characteristics are good and a specific surface area is increased, thereby increasing a reaction range of a positive electrode to allow implementation of a high capacity. Accordingly, a lithium-air battery having high output and high capacity characteristics may be implemented.

Hereinafter, the present invention will be described in detail by the examples. However, the examples are for describing the present invention in more detail, and the scope of the present invention is not limited to the following examples.

\<Example\> Preparation of Reduced Acylated Graphene Oxide and Manufacture of Lithium Secondary Battery Including the Same

1. Preparation of Acylated Graphene Oxide (AGO)

Acylated graphene oxide particles were prepared using graphene oxide obtained by a modified Hummers method as a precursor.

Specifically, 2 g of graphene oxide (GO) was mixed with 2 g of an acetyl anhydride (99%, Sigma-Aldrich) to prepare an acylated graphene oxide dispersion (black). Thereafter, the acylated graphene oxide dispersion was reacted at 120° C. for 5 hours to prepare an acylated graphene oxide mixed solution (black). Next, the acylated graphene oxide mixed solution reacted above was washed repeatedly with D.I. Water using a centrifuge to adjust the pH to 5. After completing the washing, filtration under reduced pressure was performed to obtain a solid paste, which was dried at 60° C. for 24 hours in a vacuum chamber to obtain powdery acylated graphene oxide.

2. Preparation of Reduced Acylated Graphene Oxide (RAGO)

1 g of acylated graphene oxide obtained by the acylation reaction was mixed with 0.1 g of Super-p using a mortar. The mixed powder was subjected to a reduction reaction 6 times for 10 seconds each at 800 W power in a microwave to obtain powdery reduced acylated graphene oxide.

3. Manufacture of Negative Electrode Including Reduced Acylated Graphene Oxide Acylated graphene oxide was used as a negative electrode active material. Super-P (TIMICAL Graphite and Carbon) as a conductive material and CMCSBR as a binder were dissolved to prepare a mixture at a weight ratio of 8 (active material):1 (conductive material):1 (binder). At this time, as the CMCSBR, CMCSBRs having different wt % from each other were prepared by adjusting the viscosity with D.I. water considering the specific surface area of each powder to manufacture an electrode.

The active material and the conductive material were mixed for 30 minutes, and a CMCSBR solution having an adjusted viscosity was added thereto to prepare a slurry. Thereafter, casting was performed on a copper foil with the thickness adjusted by a glass rod. The electrode was dried in an oven at 70° C. for 12 hours, and a roll press was used to perform rolling to 80% of the electrode thickness to manufacture a negative electrode.

4. Manufacture of Lithium Secondary Battery Including Negative Electrode

The negative electrode was disposed on the lower end, and a SK membrane was used as a separator. A gasket was put therein in order to entirely fix the separator, and then 0.5 t of lithium metal as a counter electrode was disposed on the upper end. 2 uL of 1.0 M $LiPF_6$-ethylene carbonate (Ec)/ diethylene carbonate (DEC) (1:1 volume ratio) as an electrolyte solution was injected into the middle. 0.5 t of spacer was put therein in order to adjust the thickness in the electrode. Finally, a wave spring was disposed so that an empty space does not exist between the separators, thereby manufacturing a 2032 type coin half cell. The assembly process of the battery was performed in a glove box filled with argon gas.

<Comparative Example 1> Manufacture of Lithium Secondary Battery Including Graphite A lithium secondary battery was manufactured in the same manner as in Example, except that commercial graphite was used instead of the reduced acylated graphene oxide.

<Comparative Example 2> Manufacture of Lithium Secondary Battery Including Reduced Graphene Oxide (RGO)

1.0 g of graphene oxide was mixed with 0.1 g of Super-p. The mixture was transferred to a microwave, and was subjected to a reduction reaction 6 times for 10 seconds each for 1 minute at 800 W power. After drastic heat reduction, it was confirmed that the color of the product was changed from yellow to black, and the volume of a graphene nanosheet was also greatly expanded. When reduction was completed, graphene powder was dispersed in D.I. Water, and then a sonification treatment was performed with ultra-sonification in order to change it into a shape-controlled graphene nanosheet. After an energy induction process, graphene powder was dried for 24 hours in a vacuum chamber at room temperature to prepare reduced powdery graphene oxide.

A lithium secondary battery was manufactured in the same manner as in Example, except that the reduced graphene oxide prepared above was used instead of the reduced acylated graphene oxide prepared in Example.

<Experimental Example 1> Analysis of Microstructure of Reduced Acylated Graphene Oxide

1. SEM Analysis

The microstructures of the materials prepared in the example and the comparative examples were observed by SEM.

Figure 2:
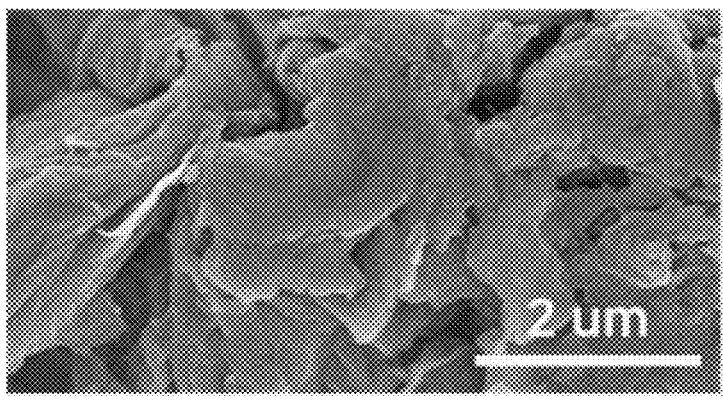
FIG. 2 is scanning electron microscope (SEM) photographs in which GO is observed.
Figure 3:
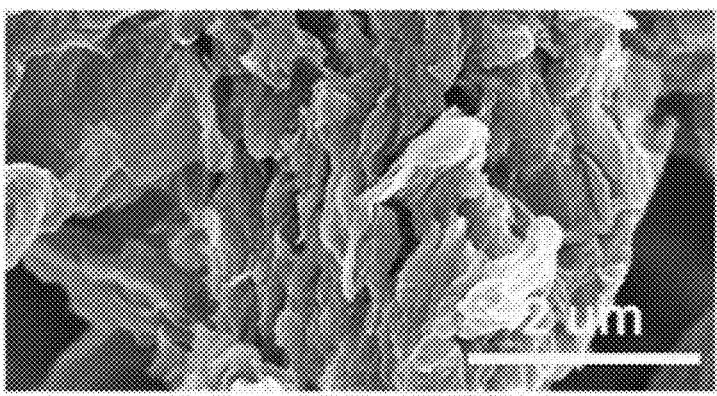
FIG. 3 is scanning electron microscope (SEM) photographs in which AGO is observed.
Figure 4:
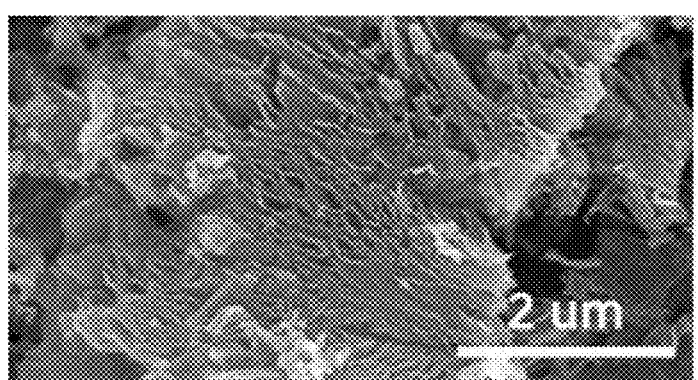
FIG. 4 is scanning electron microscope (SEM) photographs in which RGO is observed.
Figure 5:
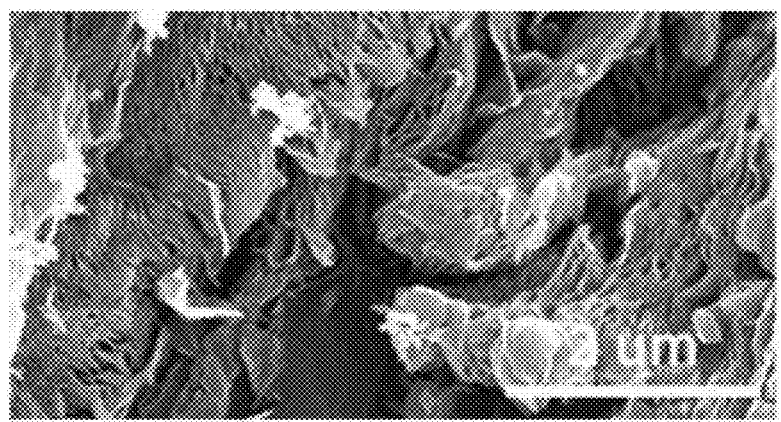
FIG. 5 is scanning electron microscope (SEM) photographs in which RAGO is observed.

FIG. 2 is an SEM image of graphene oxide (GO), FIG. 3 is an SEM image of acylated graphene oxide (AGO), FIG. 4 is an SEM image of reduced graphene oxide (RGO), and FIG. 5 is an SEM image of acylated graphene oxide (RAGO). Referring to FIG. 2 to FIG. 5, considering that acylated graphene oxide has a more wrinkled material surface and more layered flakes than graphene oxide, it is recognized that the acylated graphene oxide has a higher oxidation state. In addition, it was confirmed that a material with thin sheets accumulated was formed in Example (RAGO) and Comparative Example 2 (RGO) after the reduction process, and in Example (RAGO), the layer thickness was similar to that of Comparative Example 2 (RGO), but has a distance between layers formed densely.

2. TEM Analysis

The microstructures of the materials prepared in the example and the comparative examples were observed by TEM.

Figure 6:
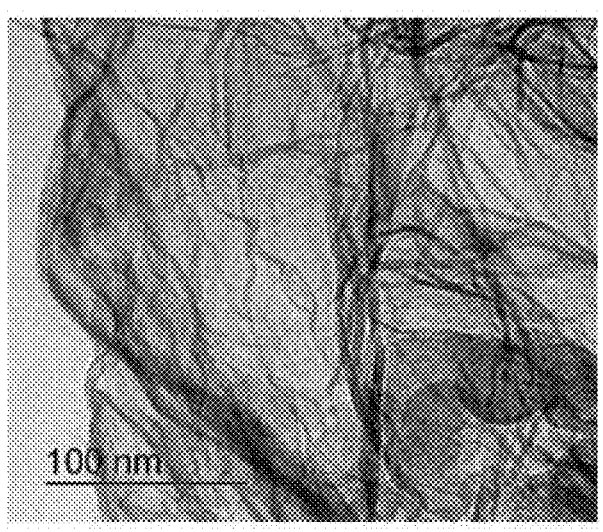
FIG. 6 is transmission electron microscope (TEM) photographs in which RGO at low magnification.
Figure 7:
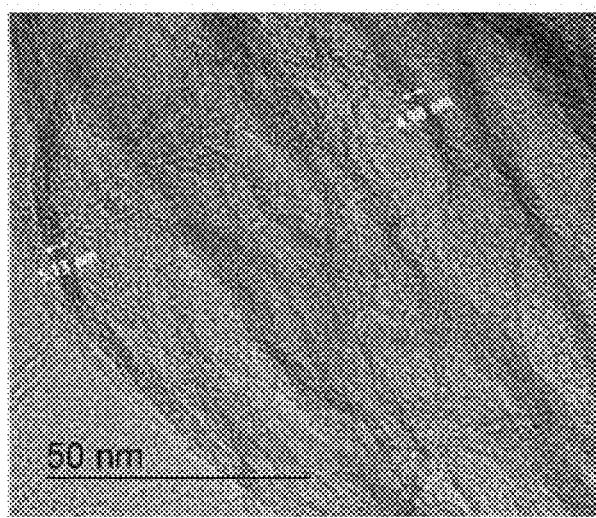
FIG. 7 is transmission electron microscope (TEM) photographs in which RGO at high magnification.
Figure 8:
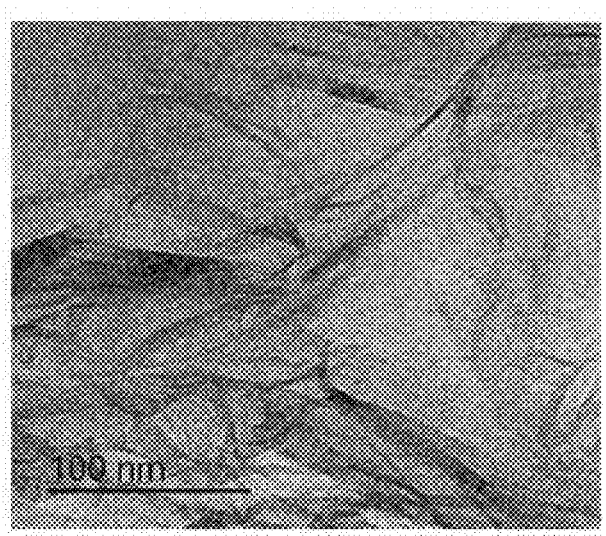
FIG. 8 is transmission electron microscope (TEM) photographs in which RAGO at low magnification.
Figure 9:
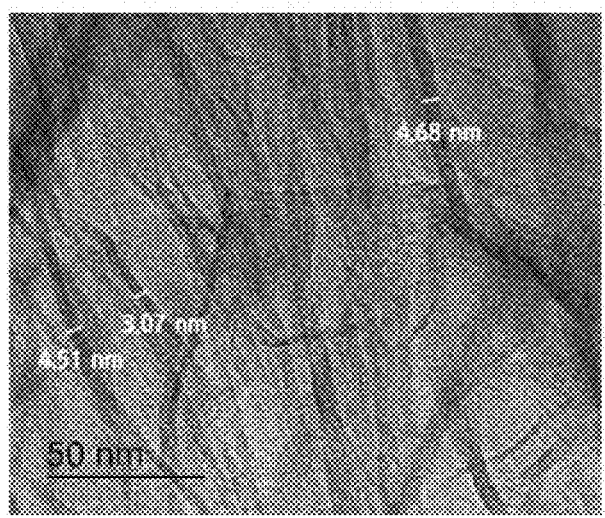
FIG. 9 is transmission electron microscope (TEM) photographs in which RAGO at high magnification.

FIG. 6, and 7 are TEM images of reduced graphene oxide (RGO), and FIGS. 8 and 9 are TEM images of reduced acylated graphene oxide (RAGO). Referring to FIGS. 6 to 9, it is seen that a graphene layer is formed well by a reduction reaction, and as a result of measuring an average thickness of the graphene layer of each material, the thickness of Example (RAGO) was 4.1 nm, which is thinner than the thickness of Comparative Example 2 (RGO) which was 5.1 nm.

3. XRD Analysis

The microstructures of the materials prepared in the example and the comparative examples were observed by XRD.

An interlayer spacing between graphite layers is an ideal indicator showing an oxidation degree of graphene oxide. It is expected that the larger the interlayer spacing is, the higher the oxidation degree is.

The space in each active material sheet was calculated using Bragg's law expressed by the following equation:

$$2d \sin \theta = n\lambda$$

wherein d is a distance between diffraction planes, θ is an incidence angle, n is an integer, and λ is an X-ray wavelength.

Figure 10:
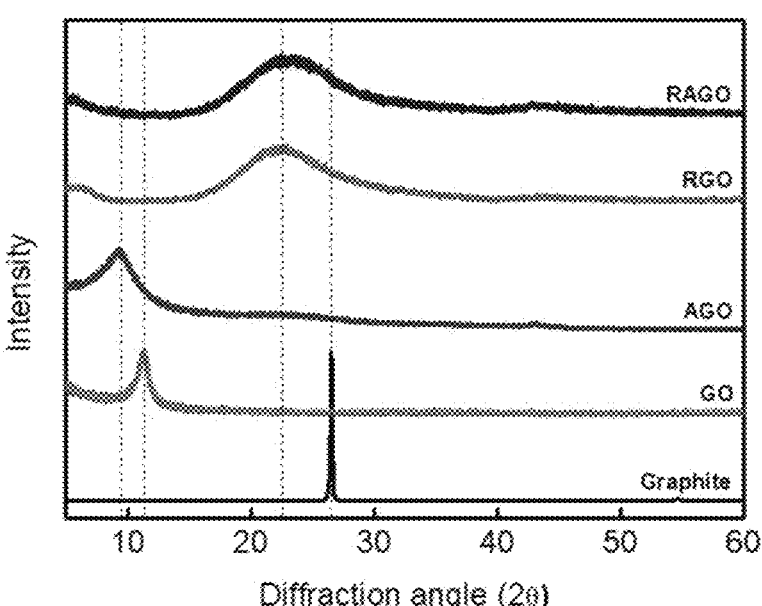
FIG. 10 is a graph showing XRD patterns of GO, AGO, RGO, and RAGO.

Referring to FIG. 10, the interlayer spacing of acylated graphene oxide (AGO) which was 0.95 nm (9.15°) was larger than that of graphene oxide (GO) which was 0.80 nm (11.4°). It was found therefrom that AGO prepared by the acylation reaction had a higher oxidation state so that more functional groups are present by the introduction of an acyl group, thereby forming an open structure. The open structure as such imparts an additional capacity to make the active material easy to have high energy characteristics, but a lot of irreversibility occurs due to the increase in the specific surface area by the open type structure, so that initial efficiency is low, and thus, there is limitation to apply it as a secondary battery active material. In addition, many oxygen functional groups are included inside due to the high oxidation degree so that electronic conductivity is low, and when it is applied as a secondary battery active material, conductivity is low, and thus, it is expected that AGO is a material inappropriate for improvement of the rate-limiting characteristics of a battery.

However, in Comparative Example 2 (RGO) and Example (RAGO) after the reduction process, considering that the spacing was decreased to be smaller than the interlayer spacings of GO and AGO, it is recognized that the functional groups containing oxygen were removed and an sp² structure was established again, and a large amorphous peak was shown. This was a structure which was more open than graphite, but has decreased openness as compared with GO and AGO to lower the ratio of the irreversible capacity and increase the capacity. As the openness is decreased so that the structure is closer to that of graphite, the efficiency in the high capacity material is increased to increase the life characteristics.

More specifically, the interlayer spacings of Example (RAGO) and Comparative Example 2 (RGO) were 0.38 nm (23.48°) and 0.39 nm (22.91°), respectively, and the, the interlayer spacing of Example was calculated to be smaller than that of Comparative Example 2. This means that as the functional groups containing oxygen are removed in the process of introducing an acyl group to GO to reduce the structure back from the open structure, an internal repulsive force is decreased to decrease the distance, so that the shape is returned to a similar shape to graphite. However, the effect of increasing the interlayer spacing by 0.04 nm was greater than that of Comparative Example 1 (graphite) having the interlayer spacing of 0.34 nm (36.52°). This shows that the action to increase the capacity of the active material was effective by increasing the interlayer spacing.

Additionally, the size of the crystallite of each active material and the number of graphene layers were determined using the following Scherrer equation:

$$L_c\beta \cos \theta = 0.89\lambda$$

wherein $L_C$ is a size of a crystallite in a direction of axis a, $\beta$ is a width of a peak corresponding to a half value of a maximum height of the peak, and $\lambda$ is a wavelength of an X-ray.

The number of graphene layers of Example (RAGO) was 5.6, which was greater than that of Comparative Example 2 (RGO) which was 5.5. It was found therefrom that the oxygen functional groups of Example were removed better, and thus, the interlayer spacing was smaller than that of Comparative Example 2 so that the number of the layers was increased.

The size of the crystallite of the material, d-spacing, and the number of layers is shown in the following Table 1:

TABLE 1

| Material | 2Θ (°) | $L_C$ (nm) | d-spacing (nm) | Number of layers |
|---|---|---|---|---|
| Comparative Example 1 (graphite) | 26.52 | 48.39 | 0.34 | 142.3 |
| GO | 11.4 | | 0.80 | |
| AGO | 9.15 | | 0.95 | |
| Comparative Example 2 (RGO) | 22.91 | 2.15 | 0.39 | 5.5 |
| Example (RAGO) | 23.48 | 2.12 | 0.38 | 5.6 |

4. RAMAN Analysis

The microstructures of the materials prepared in the example and the comparative examples were observed by RAMAN.

Figure 11:
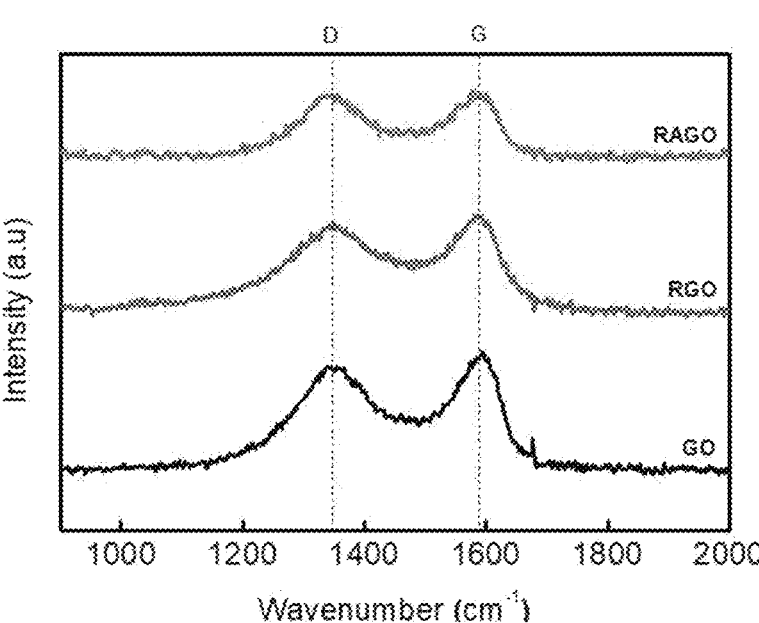
FIG. 11 is a graph showing Raman spectra of GO, RGO, and RAGO.

Referring to FIG. 11, characteristic peaks were observed at 1350 cm⁻¹ and 1580 cm⁻¹ corresponding to D and G bands, respectively in the Raman spectrum of graphene. The G band shows plane stretching between sp² carbon atoms, and the D band shows a disordered band caused by structural and edge defects. Therefore, an intensity ratio of the D band to the G band (ID/IG) is a means for measuring an average size and a disorder degree of the sp² carbon region in graphite.

It was confirmed that the ID/IG ratio was increased to 0.887, 0.914, and 0.980 by the increase in the defects in the order of GO, Comparative Example 2 (RGO), and Example (RAGO). It was found therefrom that when an acyl group is introduced, distortion is increased by a repulsive force to each other by a negative charge, and defects in a carbon lattice are increased to decrease the size of an sp² domain, so that the ID/IG ratio was increased.

The position of the G band was shifted from 1594.2 cm⁻¹ to 1575.8 cm⁻¹ in the order of Comparative Example 2 (RGO) and Example (RAGO) after the reduction process in GO. This means that a conjugated π system was restored so that an interaction between conjugated carbon double bonds became more similar to the aromatics. That is, the increase of the ID/IG ratio and the reduction of GO were due to the decrease in an average size of RGO sheets and the restoration of numerous graphite domains in the amorphous region of GO. Therefore, the shift of the G band and the increase in ID/IG ratio mean that the sp² domain was successfully restored in the graphene structure.

The position of the band and the ID/IG ratio of each material are shown in the following Table 2:

TABLE 2

| Material | Center of D band (cm⁻¹) | Center of G band (cm⁻¹) | ID/IG |
|---|---|---|---|
| GO | 1339.6 | 1594.2 | 0.887 |
| Comparative Example 2 (RGO) | 1349.2 | 1582.6 | 0.914 |
| Example (RAGO) | 1348.3 | 1575.8 | 0.980 |

5. FT-IR Analysis

The microstructures of the materials prepared in the example and the comparative examples were observed by FT-IR.

Figure 12:
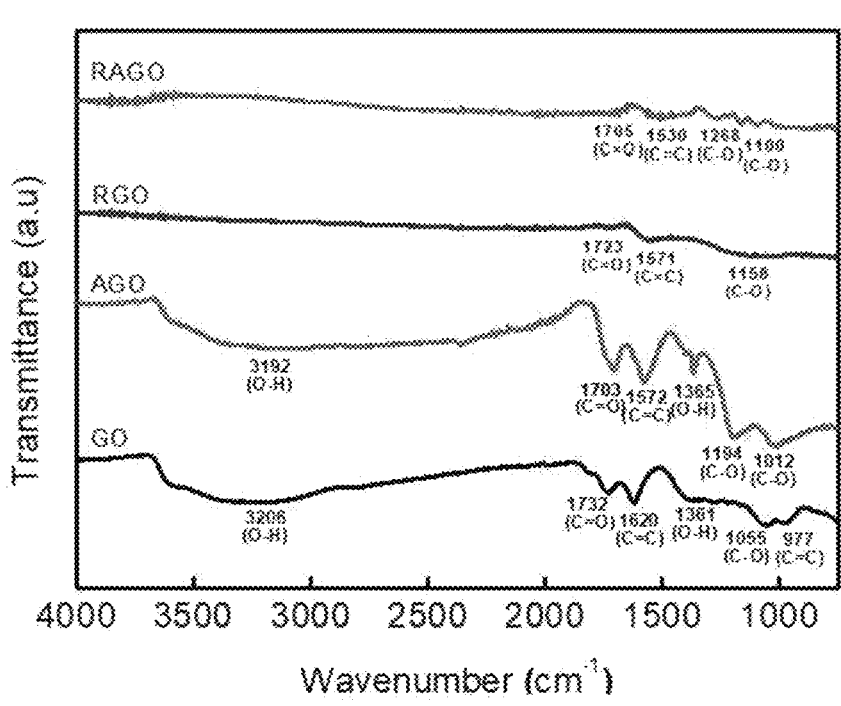
FIG. 12 is a graph showing FT-IR spectra of GO, AGO, RGO, and RAGO.

Referring to FIG. 12, the peaks at 3206, 1732, 1620, 1361, and 1055 cm⁻¹ which were the typical FT-KR spectra of GO correspond to an OH group, C=O and C=C of COOH, —OH of C—OH, and C—O of a COC (epoxy) functional group. These characteristics mean that there is a functional group containing a large amount of oxygen by an oxidation reaction of graphite as a precursor. Thus, oxygen was occupied a lot in the edge and a basal surface of GO, and thus, it was confirmed that GO was successfully synthesized.

As compared with GO, in Comparative Example 2 (RGO), oxygen was removed to remove an OH group, and the peaks of other functional groups disappeared or the intensity of the peak was weakened. It was found therefrom that the functional groups containing oxygen were minimally included due to the reduction reaction of GO.

In Example 1 (RAGO), it was seen that AGO made by the acylation reaction was reduced again, thereby removing an acyl group part having weak binding energy, which was bonded to the edge when the functional groups containing oxygen were removed, so that the peaks disappeared or the intensity was much weakened in a similar manner to Comparative Example 2 (RGO).

6. XPS Analysis

The microstructures of the materials prepared in the example and the comparative examples were observed by XPS in a C is binding energy range.

Figure 13:
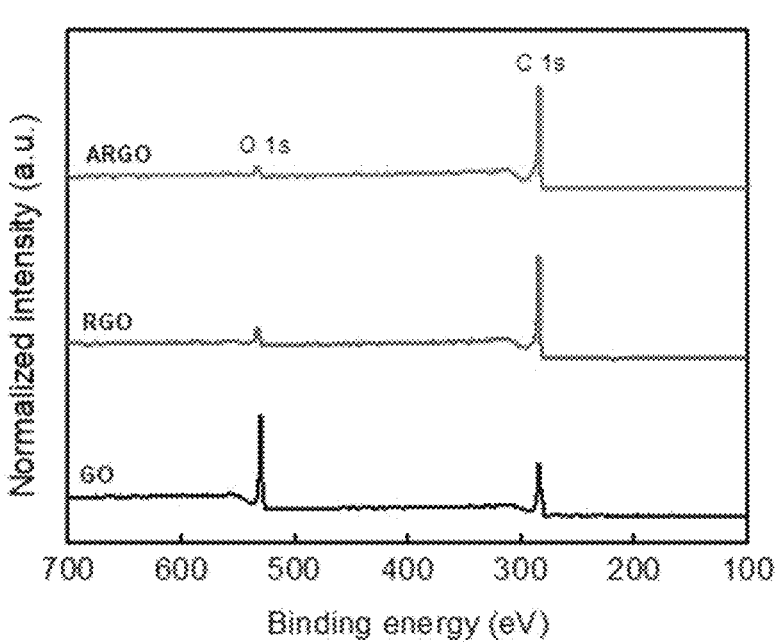
FIG. 13 is graphs showing XPS patterns of GO, RGO, and RAGO.

Referring to FIG. 13, two peaks corresponding to carbon (C 1s) and oxygen (O 1s) may be seen in GO, RGO, and RAGO.

Figure 14:
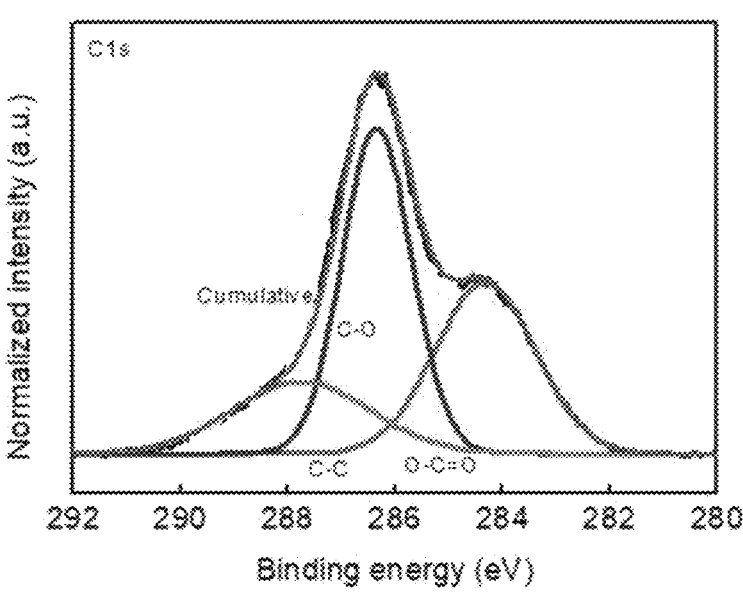
FIG. 14 is graphs showing XPS patterns of GO.

More specifically, referring to FIG. 14 corresponding to GO, these may be divided into three peaks positioned at 284.7, 286.2, and 288.9 eV corresponding to C—C/C=C, C—O/C=O, and O—C=O bonds, respectively. The main oxygen-containing functional groups in GO are spa carbon, that is, C—O, an epoxy bond, carbonyl (C=O), and a hydroxyl group (C—OH). It was confirmed that the peak of the C—O bond has a higher intensity than the peak of the C—C bond by the oxidation process of graphite, so that the oxidation reaction was performed.

Figures 15, 16:
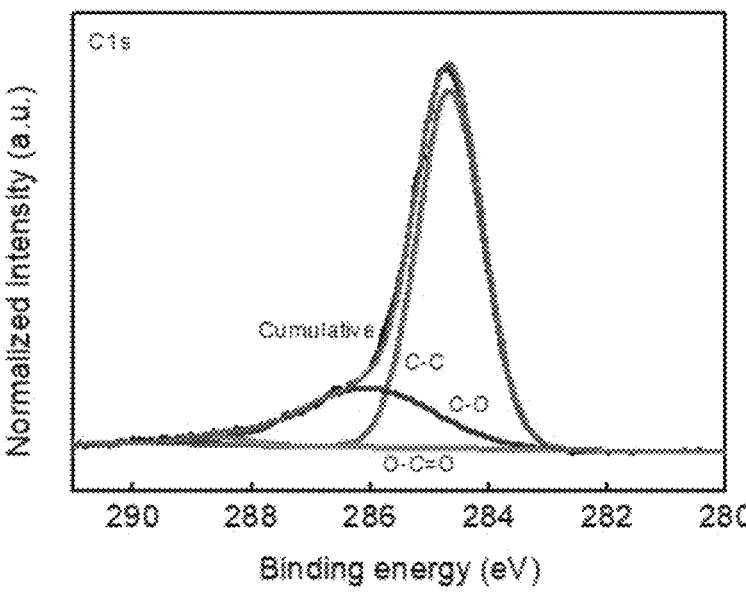
FIG. 15 is graphs showing XPS patterns of RGO.
FIG. 16 is graphs showing XPS patterns of RAGO.

Referring to FIG. 15 corresponding to Comparative Example 2 (RGO), a strong peak is shown at about 284.7 eV assigned to a carbon atom and sp$^2$-hybrid carbon bonded to oxygen by a single bond or a double bond. The peak at 284.7 eV means that most of the carbon atoms are arranged in a conjugated honeycomb grid. In addition, considering that the C—O peak was decreased as compared with GO and the C/O ratio was increased from 0.564 to 5.210, it was confirmed that the functional groups containing oxygen were removed well in the reduction process.

Referring to FIG. 16 corresponding to Example (RAGO), a strong peak is shown at about 284.7 eV assigned to a carbon atom and sp$^2$-hybrid carbon bonded to oxygen by a single bond or a double bond. The peak at 284.7 eV means that most of the carbon atoms are arranged in a conjugated honeycomb grid. The C—O binding and O—C=O binding peaks were decreased more than in Comparative Example 2 (RGO), and this may be confirmed also in the C/O ratio. Thus, it was found that most of the functional groups containing oxygen were removed by the reduction process.

The C/O ratio of each material is shown in the following Table 3.

TABLE 3

| Material | C/O ratio |
|---|---|
| GO | 0.564 |
| Comparative Example 2 (RGO) | 5.210 |
| Example (RAGO) | 9.395 |

As the degree of including the oxygen functional group in a GO series was increased, the electronic conductivity was lowered. This is because electrical instability is increased due to mutual electrostatic repulsive force of hydroxyl groups positioned close to each other in a material including an oxygen functional group a lot such as GO and AGO. Therefore, removal of the oxygen functional group is appropriate for implementing improvement of rate-limiting characteristics by high electronic conductivity in a lithium secondary battery. Therefore, in GO and AGO, the capacity may be increased, but rate-limiting characteristics becomes poor, and thus, Comparative Example 2 (RGO) and Example (RAGO) which have structures obtained by reducing GO and AGO are materials appropriate for the rate-limiting characteristics.

7. Particle Size and Tap Density Analysis

The particle size and the tap density of the material prepared in the example and the comparative examples were analyzed.

Figure 17:
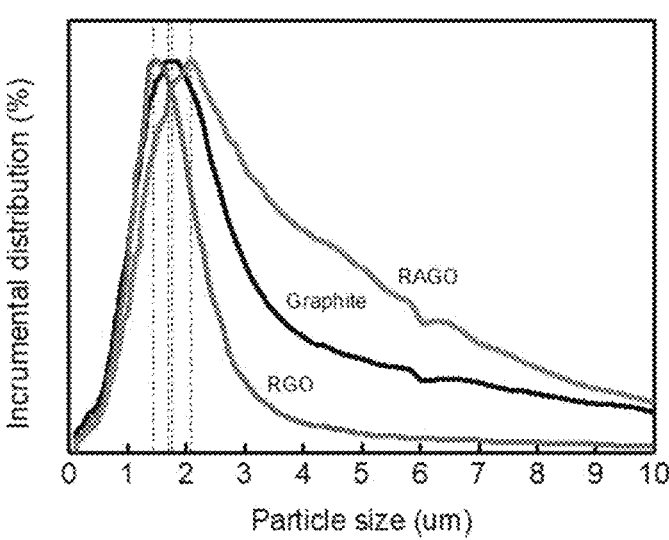
FIG. 17 is graphs showing particle sizes of graphite, RGO, and RAGO.

Referring to FIG. 17, the average particle size of Comparative Example 2 (RGO) was the smallest at 1.49 μm, and the particle size of Example (RAGO) was increased to 2.28 μm. In addition, Example had the largest particle size distribution so that particles having various sizes existed.

Figure 18:
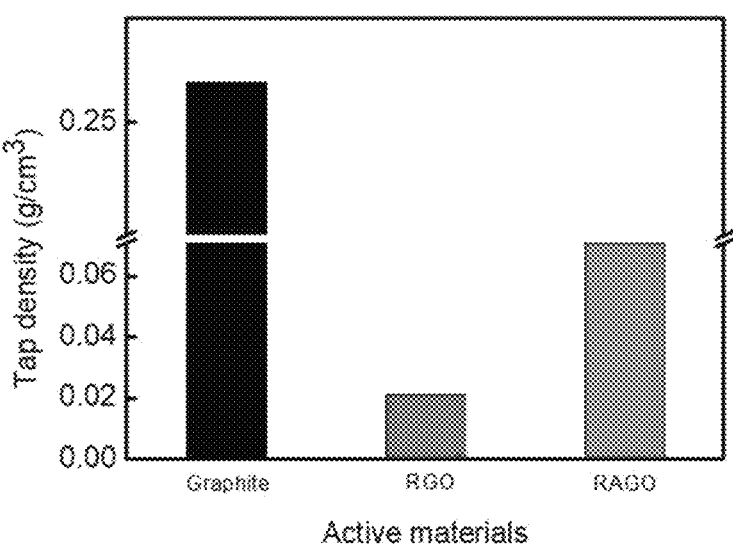
FIG. 18 is graphs showing tap densities of graphite, RGO, and RAGO.

Referring to FIG. 18, the tap density of Example (RAGO) was 0.071 g/cm$^3$, which was increased by three times or more than Comparative Example 2 (RGO) having the tap density of 0.021 g/cm$^3$. This is because the particle size distribution of Example was large, so that small particles may densely exist between big particles. Since the increase in the tap density as such may increase volume energy density, it is one of important requirements in the manufacture of a high-energy lithium ion battery. The high tap density may provide a higher volume capacity, a thinner electrode, and a shorter electron path for the same mass load.

The average particle size and the tap density values of the materials are shown in the following Table 4:

TABLE 4

| Material | Average particle diameter (μm) | Tap density (g/cm$^3$) |
|---|---|---|
| Comparative Example 1 (graphite) | 1.78 | 0.263 |
| Comparative Example 2 (RGO) | 1.49 | 0.021 |
| Example (RAGO) | 2.28 | 0.071 |

8. Analysis of Surface Area by BET

The surface areas of the materials prepared in the example and the comparative examples were analyzed by BET.

Figure 19:
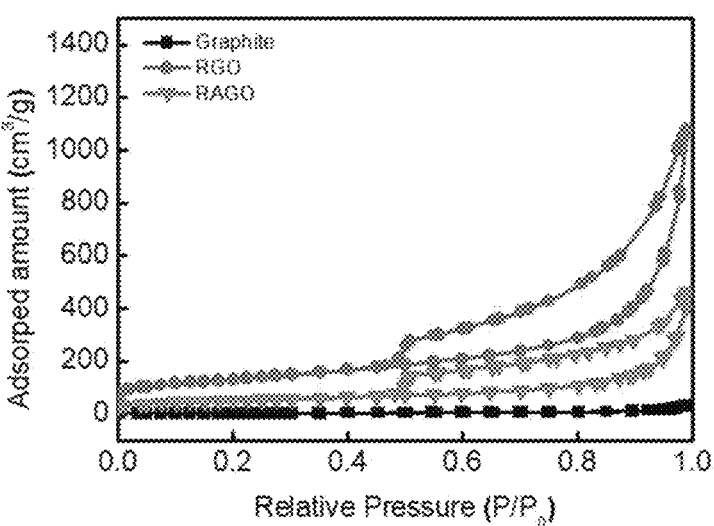
FIG. 19 is graphs showing measurements of BET of graphite, RGO, and RAGO.

FIG. 19 shows N2 adsorption/desorption isotherms of the active materials. Referring to FIG. 19, it is seen that there was almost no pore structure in graphite. Comparative Example 2 (RGO) and Example (RAGO) are IV type isotherms having hysteresis at a high partial pressure and show porous characteristics.

More specifically, the specific surface area and the pore volume of graphite were measured as 11.04 m$^2$/g and 0.050 cm$^3$/g, but the specific surface area and the pore volume of RGO prepared by oxidizing and then reducing graphite were greatly increased to 467.2 m$^2$/g and 1.648 cm$^3$/g, respectively.

Example (RAGO) had the specific surface area (a$_s$, BET) and the pore volume (Vp) of 173.24 m$^2$/g and 0.660 cm$^3$/g, which were decreased as compared with Comparative Example 2 (RGO), but were increased as compared with Comparative Example 1 (graphite) which were 11.04 m$^2$/g and 0.050 cm$^3$/g. A surface area larger than that of Comparative Example 1 shows a larger electrode-electrolyte contact area and rapid diffusion of electrolyte ions. This imparts high rate-limiting characteristics in Comparative Example 2 and Example 1 than Comparative Example 1. In addition, a larger pore volume may be advantageous for accepting volume change, and provides more active sites during charging and discharging, resulting in better cycling stability. In addition, it was found that after an acyl group was introduced by the specific surface of Example, the structure returned to the structure similar to Comparative Example 1. This may have a decreased capacity as compared with Comparative Example 2, but suppresses an initial electrolyte decomposition reaction occurring in a large specific surface area to minimize an irreversible capacity loss in an initial cycle and is advantageous for long-term cycle characteristics.

Figure 20:
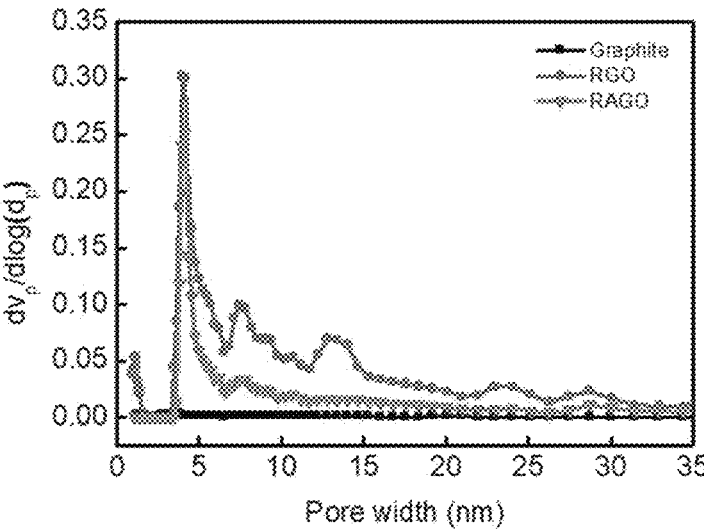
FIG. 20 is graphs showing measurements of BET of graphite, RGO, and RAGO.

FIG. 20 shows the pore-size distribution of the prepared active materials. Referring to FIG. 20, it was found that in Comparative Example 2, pores having various sizes were formed from 5 nm as a starting point. However, Example had a relatively uniform pore size.

The BET specific surface area, the pore volume, and the pore diameter measured are shown in the following Table 5:

TABLE 5

| Material | $a_s$, BET $(m^2/g)$ | Vp $(cm^3/g)$ | Dp (nm) |
|---|---|---|---|
| Comparative Example 1 (graphite) | 11.04 | 0.050 | 18.0 |
| Comparative Example 2 (RGO) | 467.2 | 1.648 | 14.1 |
| Example 1 (RAGO) | 173.2 | 0.660 | 15.2 |

<Experimental Example 2> Analysis of Electrochemical Properties of Lithium Secondary Battery Including Reduced Acylated Graphene Oxide 1. Impedance Measurement The impedance of a lithium coin half cell manufactured using the material prepared in the example and the comparative examples in a frequency range of 100 kHz to 0.01 Hz as a negative electrode active material was measured.

Figure 21:
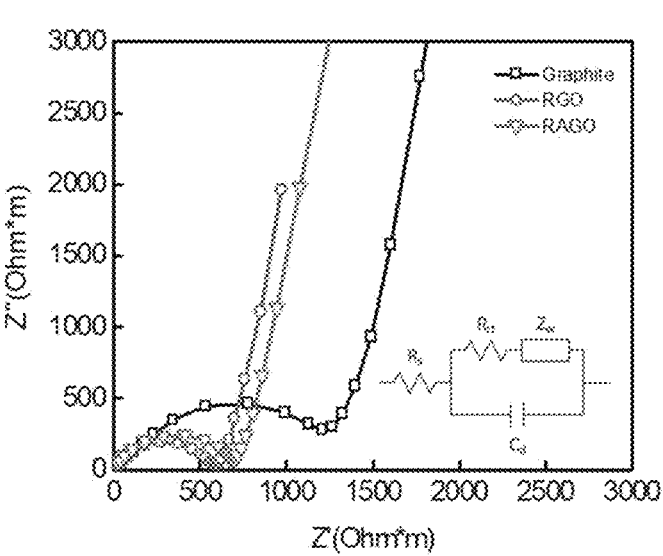
FIG. 21 is drawings showing the results of measuring impedance including graphite, RGO, and RAGO as a negative electrode active material with equivalent electric circuit.

In FIG. 21, an equivalent circuit obtained from an EIS experiment in a typical secondary battery was depicted. The equivalent circuit is formed of three resistance components, and first, Rs shown in a high frequency range is related to electrolyte resistance, and $R_{ct}$ shows charge transfer resistance in an electrode. A slope of 45° part of the curve in the middle frequency range refers to Warburg resistance ($Z_w$) representing ion diffusion/transport of an electrolyte. A Nyquist plot showing impedance behavior of a porous electrode in an open circuit potential is indicated in FIG. 21. All resistance is shown as a non-resistance value considering the thickness and the weight of the electrode.

Figure 22:
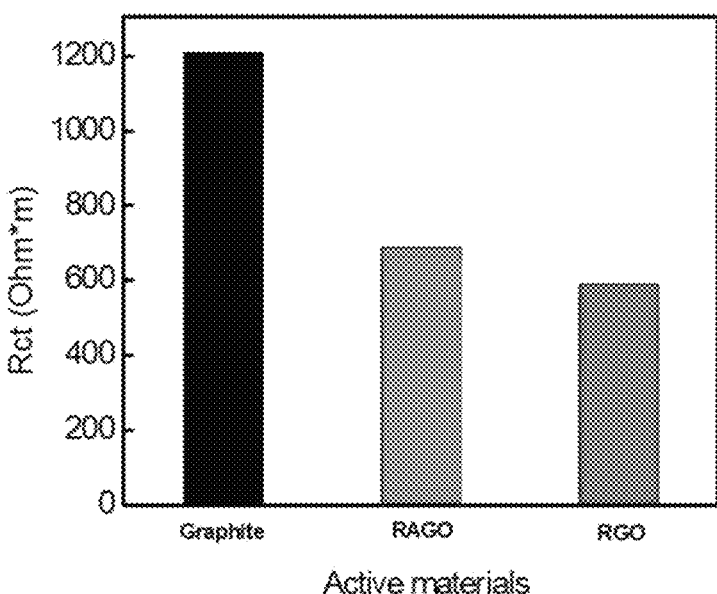
FIG. 22 is drawings showing a charge transfer resistance obtained from FIG. 21 of batteries including graphite, RGO, and RAGO as a negative electrode active material.

As seen from FIG. 22 and Table 6, the charge transfer resistance ($R_{ct}$) of Example was 690 Ohm*m, which is a little higher than that of Comparative Example 2 which was 592 Ohm*m. This is because the specific surface area of Example was decreased as compared with Comparative Example 2, as seen from the BET analysis results. However, it was decreased as compared with Comparative Example 1 which was 1209 Ohm*m. The increase in the conductivity by the acylation reaction as such lowers total resistance, which is advantageous for high rate-limiting characteristics of a composite.

TABLE 6

| Material | RS (Ohm*m) | $R_{ct}$ (Ohm*m) |
|---|---|---|
| Comparative Example 1 (graphite) | 42 | 1209 |
| Comparative Example 2 (RGO) | 25 | 592 |
| Example (RAGO) | 16 | 690 |

2. Analysis of Cycle Characteristics

For evaluating the electrochemical properties of the synthesized material, the materials prepared in the example and the comparative examples were used as an electrode material to perform charge and discharge and speed performance tests at 0.002 V to 2.5 V with a coin-type half cell. Generally, since the first discharge capacity of the battery is known to be related to the formation of a solid electrolyte interface (SEI), the capacity at the second cycle was regarded as an initial capacity.

Figure 23:
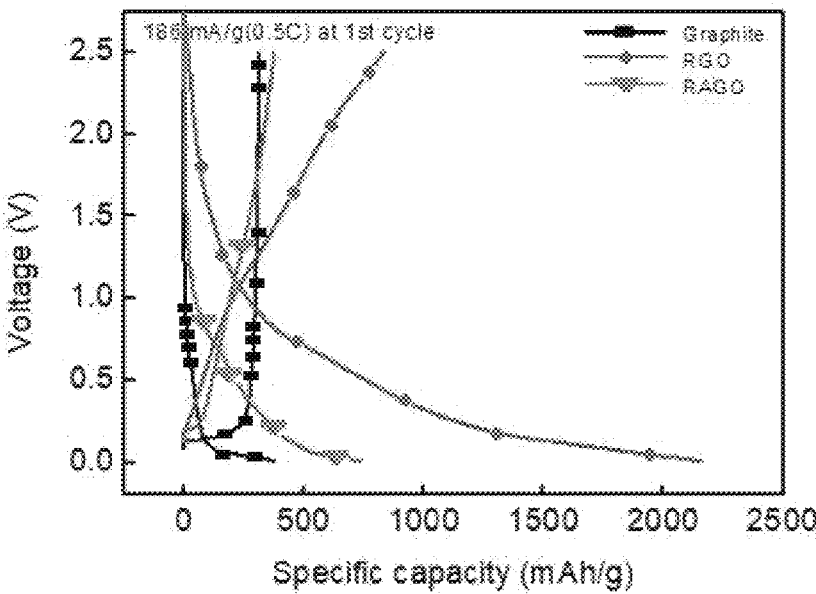
FIG. 23 is drawings showing voltage profile of a lithium half battery including graphite, RGO, and RAGO as a negative electrode active material.

As seen in FIG. 23, the potential flat area of the negative electrode of Comparative Example 2, which was due to the electrolyte decomposition reaction and determines an initial irreversible capacity loss, started from the start of charging. However, it was found that the negative electrode of Example had a potential flat area formed from the 1.2 V ($Li^+/Li$) part had a similar shape to Comparative Example 1. This is because the specific surface area of the negative electrode of Example was smaller and a part of the active site was removed from the surface during the reduction process, thereby decreasing the irreversible side reaction leading to the formation of a SEI layer. The decreased irreversible side reaction will contribute to the improvement of an initial coulomb efficiency value.

Figure 24:
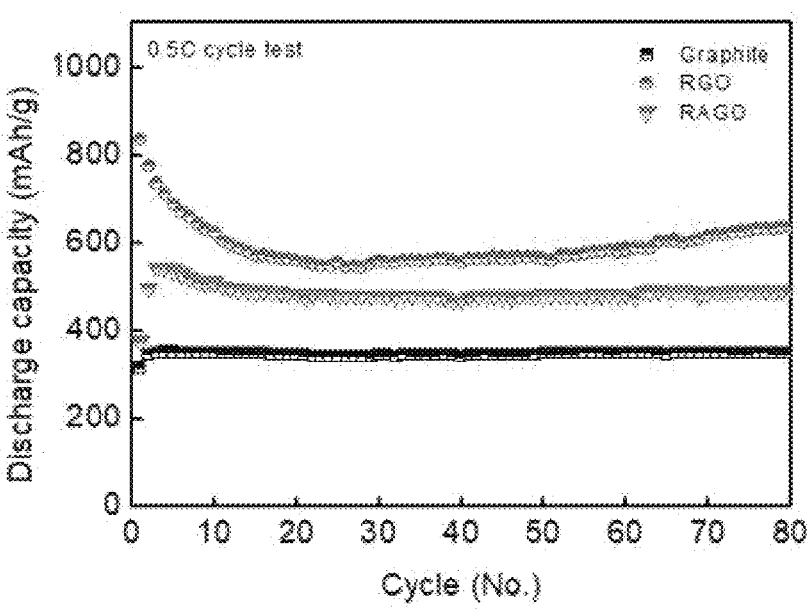
FIG. 24 is drawings showing discharge cyclability characteristics of a lithium half battery including graphite, RGO, and RAGO as a negative electrode active material.

As seen in FIG. 24, the initial discharge capacity of Example was measured as 498 mAh/g, which was decreased as compared with the initial discharge capacity of Comparative Example 2 measured as 773 mAh/s, but increased by about 150 mAh/g or more as compared with the initial discharge capacity of Comparative Example 1 which was 347 mAh/g. However, though the discharge capacity of Comparative Example 2 was significantly decreased after 80 cycles, the discharge capacity of Example was hardly changed.

The initial discharge capacity and the discharge capacity after 80 cycles of the materials are shown in the following Table 7:

TABLE 7

| Material | Initial discharge capacity (mAh/g) | Discharge capacity after 80 cycles (mAh/g) |
|---|---|---|
| Comparative Example 1 (graphite) | 347 | 348 |
| Comparative Example 2 (RGO) | 773 | 634 |
| Example (RAGO) | 498 | 493 |

3. Evaluation of Rate-Limiting Characteristics

The rate-limiting characteristics of half cells manufactured using materials prepared in the example and the comparative examples were shown.

Figure 25:
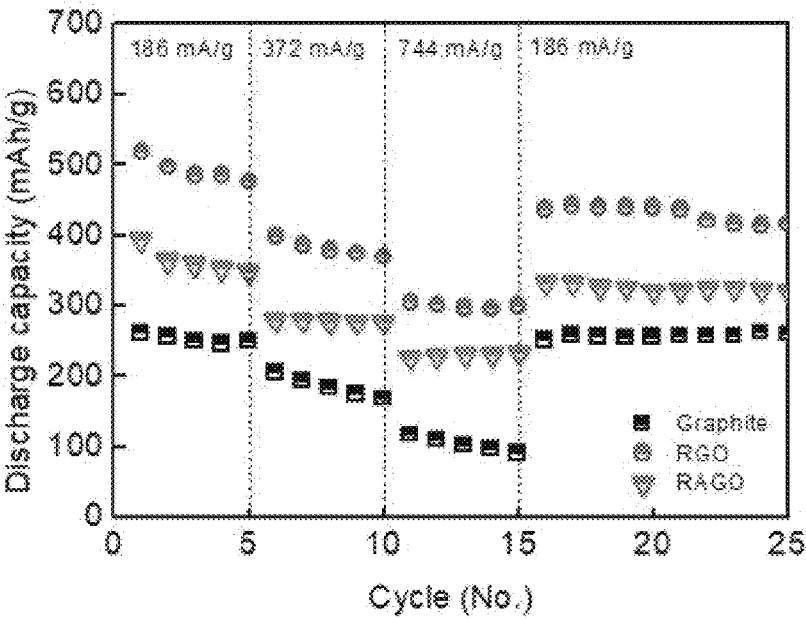
FIGS. 25, 26 and 27 are drawings showing rate-limiting characteristics of batteries including graphite, RGO, and RAGO as a negative electrode active material.
Figure 26:
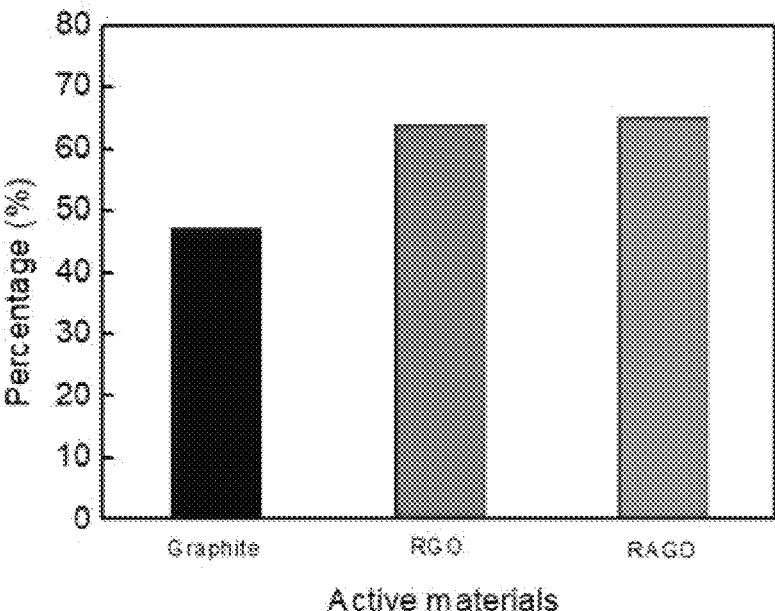

In order for charging within 20 minutes corresponding to fast charging in a lithium secondary battery to be allowed, a real capacity ratio charged with a high limited rate should be high, and as seen in FIG. 25 and FIG. 26, conventional graphite showed a charge rate of less than 50% in the same limited rate, but Comparative Example 2 and Example which are GO series showed a high charge rate of 64 and 65%. This is because as seen from the results of XRD, d-spacing larger than graphite in a GO series allows rapid insertion of $Li^+$ to improve the rate-limiting characteristics.

Figure 27:
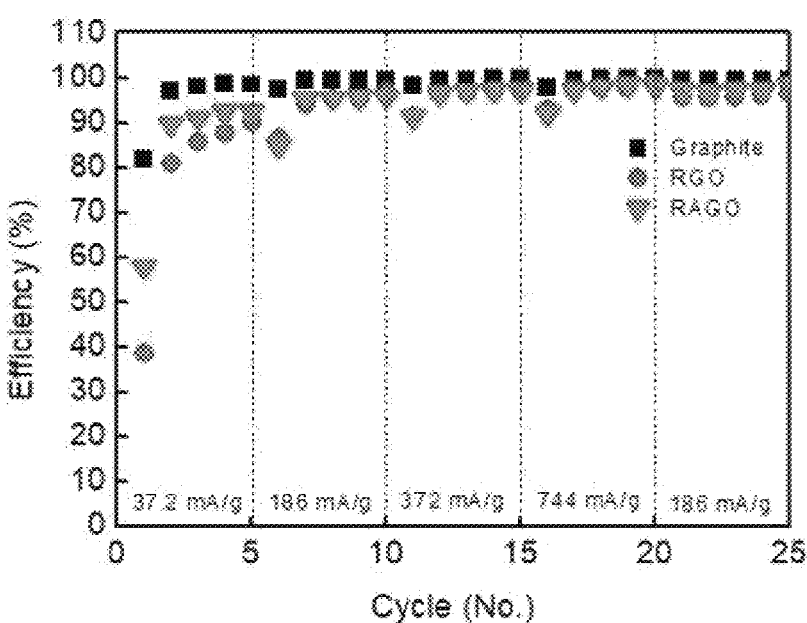

Referring to FIG. 27, the initial efficiency of the example was greatly increased from 38.7% to 58.0%, as compared with Comparative Example 2, in addition to the improvement of the rate-limiting characteristics. This is because oxygen is removed from an open structure by the acylation reaction of GO so that the specific surface area was further decreased as compared with Comparative Example 2, thereby suppressing the electrolyte decomposition reaction. In the commercially available lithium ion battery, lithium ions are supplied to a positive electrode formed of a lithium oxide, and the manufacture was performed without a carbon material as a negative electrode, and thus, it is important to minimize an irreversible capacity loss in the initial charge and discharge. From this point of view, Comparative Example 2 had a high capacity and had good rate-limiting characteristics, but low initial efficiency, and thus, was not able to be used. However, Example had good rate-limiting characteristics and had high initial efficiency even with an increased capacity as compared with Comparative Example 2, and thus, was confirmed to have a possibility of use as a negative electrode of a commercial lithium secondary battery.

The capacity ratio and the initial efficiency are shown in the following Table 8.

TABLE 8

| Material | Capacity ratio (%) of 2 C to 0.5 C | Initial efficiency (%) |
|---|---|---|
| Comparative Example 1 (graphite) | 47 | 81.9 |
| Comparative Example 2 (RGO) | 64 | 38.7 |
| Example 1 (RAGO) | 65 | 58.0 |

Referring to the experimental examples, by the method for preparing reduced acylated graphene oxide according to the present invention, a negative electrode active material for a lithium secondary battery having stable activity and a high battery capacity may be prepared with a simple and low-cost process. In addition, the active material prepared by the preparation method has low resistance, a high battery capacity, and improved rate-limiting characteristics while having stable cycle characteristics.

By the method for preparing reduced acylated graphene oxide according to the present invention, a negative electrode active material for a lithium secondary battery having stable activity and a high battery capacity may be prepared with a simple and low-cost process. In addition, the active material prepared by the preparation method has low resistance, a high battery capacity, and improved rate-limiting characteristics while having stable cycle characteristics. Here, the battery may be a redox flow battery or a lithium-air battery, as well as a lithium secondary battery.

What is claimed is:

1. A method for preparing reduced acylated graphene oxide, the method comprising:
   (a) subjecting graphene oxide to an acylation reaction to prepare acylated graphene oxide;
   (b) reducing the acylated graphene oxide; and
   wherein the acylated graphene oxide is graphene oxide bound to R—C(=O)— or R—C(=O)O—, wherein R is C1 or higher alkyl or C5 or higher aryl.

2. The method for preparing reduced acylated graphene oxide of claim 1, wherein the reducing of (b) is performed in the presence of a solid reducing agent.

3. The method for preparing reduced acylated graphene oxide of claim 2, wherein the solid reducing agent is carbonaceous powder.

4. The method for preparing reduced acylated graphene oxide of claim 3, wherein the carbonaceous powder is carbon black.

5. The method for preparing reduced acylated graphene oxide of claim 1, wherein the reducing of (b) is performed by irradiating a mixture of the acylated graphene oxide and a reducing agent with microwaves.

* * * * *